United States Patent [19]

Eggensperger et al.

[11] 4,148,905

[45] Apr. 10, 1979

[54] PRESERVING AND DISINFECTING METHOD EMPLOYING CERTAIN BIS-OXAZOLIDINES

[75] Inventors: Heinz Eggensperger, Hamburg; Karl-Heinz Diehl, Norderstedt, both of Fed. Rep. of Germany

[73] Assignee: Sterling Drug Inc., New York, N.Y.

[21] Appl. No.: 819,245

[22] Filed: Jul. 27, 1977

[30] Foreign Application Priority Data

Aug. 6, 1976 [DE] Fed. Rep. of Germany ....... 2635389

[51] Int. Cl.$^2$ .............................................. A01N 9/22
[52] U.S. Cl. .................................. 424/272; 424/248.4; 260/307 FA
[58] Field of Search .......................................... 424/272

[56] References Cited

U.S. PATENT DOCUMENTS 3,160,634 12/1964 Hodge ................................... 424/272
4,012,261 3/1977 Sidi et al. .............................. 424/272

OTHER PUBLICATIONS

Chemical Abstracts, vol. 58 (1963), p. 12750b.

*Primary Examiner*—V. D. Turner
*Attorney, Agent, or Firm*—Frederik W. Stonner; B. Woodrow Wyatt

[57] ABSTRACT

A method for preventing or retarding the growth of bacteria and fungi in a material which comprises treating the material with N,N'-methylene-bis-(oxazolidines) and -(tetrahydro-1,3-oxazines), and certain novel N,N'-methylenebis-(oxazolidines).

3 Claims, No Drawings

PRESERVING AND DISINFECTING METHOD EMPLOYING CERTAIN BIS-OXAZOLIDINES

BACKGROUND OF THE INVENTION

1. Field of the Invention

The invention relates to a method for preventing or retarding the growth of bacteria and fungi in materials such as, for example, industrial solutions, emulsions, dispersions and suspensions, which comprises treating such materials with antibacterially and antifungally effective N,N'-methylenebis(oxazolidines) or N,N'-methylenebis(tetrahydro-1,3-oxazines), and to novel N,N'-methylenebis(oxazolidines).

2. Description of the Prior Art

U.S. Pat. No. 2,647,117 discloses bis(tetrahydro-1,3-oxazino)-methanes of the formula

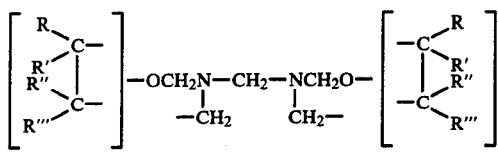

where R, R', R" and R'", inter alia, are hydrogen or alkyl. Specific compounds of the above formula which are disclosed are:

| R | R' | R" | R'" |
|---|---|---|---|
| CH$_3$ | (CH$_3$)$_3$CCH$_2$ | H | H |
| CH$_3$ | CH$_3$ | CH$_3$ | H |
| (CH$_3$)$_2$CH | (CH$_3$)$_2$CH | H | H |

The sole utility disclosed for these compounds is that they have industrial application as emulsifiers.

Rec. trav. chim. 78, 320 (1959) discloses bis(tetrahydro-1,3-oxazin-3-yl)methane. No utility is disclosed for this compound.

Chem. Abstracts 58, 12750b (1963) and J. Org. Chem. 41 (10), 1768, 1771 and 1773 (1976) disclose N,N'-methylenebis(4,4-dimethyloxazolidine). No utility is disclosed for this compound. However, the J. Org. Chem. reference teaches that this compound displays some activity against lymphocytic leukemia.

The trishydroxyalkylhexahydrotriazines, e.g. trishydroxyethylhexahydrotriazine, are well known antimicrobial agents which are prepared by reacting, in a ratio of 1:1, an alkanolamine and formaldehyde, which reactants in a ratio of 1:1.5 yield N,N'-methylenebis(oxazolidines) and -(tetrahydro-1,3-oxazines).

SUMMARY OF THE INVENTION

It has been found that N,N'-bismethylene(oxazolidine), N,N'-bismethylene(tetrahydro-1,3-oxazine) and corresponding ring alkylated derivatives possess excellent antimicrobial, i.e., antibacterial and antifungal, activity.

Thus in one aspect of the invention there is provided a method for preventing or retarding the growth of bacteria and fungi in a material susceptible to bacterial and fungal contamination which comprises treating the material with an antibacterially and antifungally effective amount of at least one compound of the formula

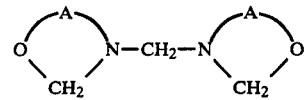

where A is alkylene selected from the group consisting of 1,2-alkanediyl having from 2 to 10 carbon atoms and 1,3-alkanediyl having from 3 to 10 carbon atoms.

In another aspect of the invention there is provided a compound selected from the group consisting of N,N'-methylenebis(oxazolidine), N,N'-methylenebis(5-methyloxazolidine) and N,N'-methylenebis(4-ethyloxazolidine).

The method of the invention is useful for preserving and disinfecting industrial solutions, emulsions, dispersions and suspensions, such as water-based paints, cold lubricating agents, adhesive solutions and dispersions, cosmetic and pharmaceutical products and aqueous formulations such as self-polishing wax emulsions and water circulation systems, e.g., cooling water circulation systems and recycled water systems used in paper manufacture.

DETAILED DESCRIPTION INCLUSIVE OF THE PREFERRED EMBODIMENTS

The compounds employed in the method of the invention can be prepared by reacting an aminoalcohol of the formula NH$_2$—A—OH, where A has the meaning defined hereinabove, with formaldehyde in the ratio of 1:1.5 to 1:2 of aminoalcohol to formaldehyde. The reaction is conveniently carried out by heating a mixture of the aminoalcohol and formaldehyde at a temperature of about 60° for about thirty minutes and subsequent removal of the water formed in the course of the reaction by azeotropic distillation. The product is then purified using standard procedures. If desired, the resulting reaction mixture can be employed directly in the method of the invention without removing the water during the reaction. However, due to the presence of the reaction water in the reaction mixture, rearrangement reactions occur which result in non-defined compounds.

The aminoalcohol starting materials belong to a well-known class of compounds which are readily available or can be readily prepared by well known procedures.

Throughout this specification, the term "1,2-alkanediyl having from 2 to 10 carbon atoms" means 1,2-ethanediyl, 1,2-ethanediyl substituted by from 1 to 4 alkyl substituents wherein the total number of carbon atoms in the combined alkyl substituents does not exceed eight, 1,3-propanediyl and 1,3-propanediyl substituted by from 1 to 6 alkyl substituents wherein the total number of carbon atoms in the combined alkyl substituents does not exceed seven.

The following examples illustrate the preparation of compounds employed in the method of the invention. The structures of the compounds were determined by infrared and nuclear magnetic resonance spectra.

EXAMPLE 1

N,N'-Methylenebis(oxazolidine)

Monoethanolamine (1 mole) was heated in a reaction flask to 60° C. with stirring and 1.5 moles paraformaldehyde was added in portions during 60 minutes. After the addition was completed, stirring at the same temperature was continued for 30 minutes. The reaction water was then distilled off. The resulting residue was distilled to give the title compound as a light colored liquid; b.p.$_{12\ mm}$=108°–110° C.; $n_{20}^D$=1.4890.

| Analysis: | CH$_2$O | | Amine | |
|---|---|---|---|---|
| | calc'd | found | calc'd | found |
| | 57% | 54.3% | 77.2% | 77.7% |

EXAMPLE 2

N,N'-Methylenebis(5-methyloxazolidine)

1-Amino-2-propanol (1 mole) was heated to 60° and 1.5 moles paraformaldehyde was added during one hour. Stirring was continued for one-half hour and the reaction mixture was cooled to room temperature. Benzene (100 ml.) was added and the reaction water was removed by azeotropic distillation. The benzene was evaporated and the resulting residue was distilled to give 85 g. of the title compound as a colorless liquid; b.p.$_{12-13\ mm}$=112°–116° C. (b.p.$_{36\ mm}$=138°–142° C.); $n_{20}^D$=1.4667.

| Analysis: | CH$_2$O | | Amine | |
|---|---|---|---|---|
| | calc'd | found | calc'd | found |
| | 48.4% | 46.2% | 80.7% | 78% |

EXAMPLE 3

N,N'-Methylenebis(4,4-dimethyloxazolidine)

2-Amino-2-methyl-1-propanol (1 mole) and 1.5 moles paraformaldehyde were refluxed in benzene. After separation of the reaction water, the solvent was distilled off. The residue was distilled to give the title compound as a colorless liquid; b.p.$_6$ $_{mm}$=116°–121° C.; $n_{20}^D$=1.4653.

| Analysis: | CH$_2$O | | Amine | |
|---|---|---|---|---|
| | calc'd | found | calc'd | found |
| | 42% | 41.3% | 83.2% | 80.1% |

EXAMPLE 4

N,N'-Methylenebis(4-ethyloxazolidine)

1.5 moles paraformaldehyde was added at 60° C. with stirring to 1 mole of 2-amino-1-butanol. After completion of addition, stirring was continued for one-half hour and the reaction water was removed. The resulting residue was distilled to give the title compound; b.p.$_6$ $_{mm}$=128°–129° C.; $n_{20}^D$=1.4653.

| Analysis: | CH$_2$O | | Amine | |
|---|---|---|---|---|
| | calc'd | found | calc'd | found |
| | 42% | 40.5% | 82.2% | 78% |

EXAMPLE 5

N,N'-Methylenebis(tetrahydro-1,3-oxazine)

1.5 moles paraformaldehyde was added during one hour to 1 mole 3-amino-1-propanol at 60° C. Benzene was added and the reaction water was removed by azeotropic distillation. The resulting residue was distilled to give the title compound; b.p.$_{12\ mm}$=131°–132° C.; $n_{20}^D$=1.4846.

| Analysis: | CH$_2$O | | Amine | |
|---|---|---|---|---|
| | calc' | found | calc'd | found |
| | 48.4% | 47.5% | 80.7% | 80.9% |

The antimicrobial activity of the compounds employed in the method of the invention were determined in a tube dilution test in accordance with the Richtlinien für die Prüfung chemischer Desinfektionsmittel der Deutschen Gesellschaft für Hygiene und Mikrobiologie (3. Auflage, 1972). The minimum inhibitory concentrations (MIC) of the compounds of Examples 1 to 5 with respect to several organisms are tabulated in Table 1.

Table 1

| | MIC (Weight-percent of compound) | | | | | | | |
|---|---|---|---|---|---|---|---|---|
| | Microorganism (see list below) | | | | | | | |
| Example No. | a | b | c | d | e | f | g | h |
| 1 | 0.01 | 0.01 | 0.02 | 0.02 | 0.01 | 0.02 | 0.04 | 0.04 |
| 2 | 0.01 | 0.02 | 0.02 | .02 | 0.02 | 0.06 | 0.06 | 0.125 |
| 3 | 0.01 | 0.03 | 0.03 | .03 | 0.02 | 0.03 | 0.125 | 0.125 |
| 4 | 0.01 | 0.01 | 0.03 | .01 | 0.01 | 0.07 | 0.1 | 0.125 |
| 5 | 0.02 | 0.03 | 0.03 | .03 | 0.02 | 0.03 | 0.06 | 0.125 | a. Staphylococcus aureus  e. Bacillus subtilis
b. Escherichia coli  f. Aspergillus niger
c. Pseudomonas aeruginosa  g. Penicillium glaucum
d. Proteus vulgaris  h. Candida albicans The efficacy of the method of the invention was demonstrated in a procedure designed to simulate actual use conditions. The procedure was as follows: Portions of 50 ml. of aqueous cooling-lubricant dilution of standard concentration (normally 4%) were prepared. A test sample was prepared for each compound to be tested by addition of the compound in appropriate use concentration to the cooling-lubricant dilution. These test samples were challenged twice weekly with 1% (0.5 ml pro 50 ml) inoculum. The titer of this inoculum was at least 10$^6$ microorganisms per ml.

At the beginning of the test 1g cast-iron chips (GU 21) was added to each test sample. To simulate actual use conditions, the cooling-lubricant dilutions were agitated during the day in 200 ml Erlenmeyer flasks in a shaker. The flasks were not shaken at night. The flasks were not stoppered to insure gas exchange. Losses of the cooling-lubricant dilution due to evaporation and sampling were made up once a week with water of 20° hardness.

Twice per week, immediately prior to a new inoculation, streaking on dextrose-agar plates was carried out. The plates were incubated at 35° C. for testing of bacteria and at 22° C. for testing of fungi; readings were made after 36 and 72 hours respectively. Growth on the plates was rated semiquantitatively from negative to positive to 3-fold positive. Cessation of the preserving action is demonstrated by massive growth, i.e. 3-fold positive growth.

The inoculum consisted of a cooling-lubricant dilution which was inoculated once a week with plate cultivated microorganisms as follows:

| Bacteria: | Yeast and fungi |
|---|---|
| Escherichia coli | Candida spec. |
| Pseudomonas aeruginosa | Rhodotorula spec. |
| Proteus vulgaris | Aspergillus spec. |
| Enterobacter aerogenes | Fusarium oxysporum |
| | Cephalosporum spec. |

The inoculum so prepared was aerated in a 35° C. water bath in inverted wash bottles in a day-night cycle. Once per week 20% of the total inoculum was discarded and made up with freshly prepared cooling-lubricant dilution to insure a concentration of microorganisms in excess of $10^6$ per ml and to avoid selective cultivation of any one microorganism.

The compounds of Examples 1, 2, 3 and 5 and the known antimicrobial agent, trishydroxyethylhexahydrotriazine (hereafter THT), were tested in the above-described test procedure. The results obtained are tabulated in Table 2.

Table 1

| Compound | Concentration (Wt. %) | Medium [a] | Days elapsed until growth |  |  |  |
|---|---|---|---|---|---|---|
|  |  |  | − | + | ++ | +++ |
| Ex. 1 | 0.15 | Dromus B (4% in $H_2O$) | >46 |  |  |  |
| Ex. 2 | 0.15 | Dromus B (4% in $H_2O$) | >46 |  |  |  |
| Ex. 5 | 0.15 | Dromus B (4% in $H_2O$) | >46 |  |  |  |
| THT | 0.15 | Dromus B (4% in $H_2O$) | 7 | 15 |  | 19 |
| Ex. 1 | 0.15 | Addix SF (4% in $H_2O$) | 35 | 38 |  | 42 |
| Ex. 2 | 0.15 | Addix SF (4% in $H_2O$) | 38 | 42 |  | 46 |
| Ex. 3 | 0.15 | Addix SF (4% in $H_2O$) | 23 | 27 |  | 30 |
| Ex. 5 | 0.15 | Addix SF (4% in $H_2O$) | >46 |  |  |  |
| THT | 0.15 | Addix SF (4% in $H_2O$) | 15 |  | 18 | 21 |
| Ex. 1 | 0.15 | Oemeta (4% in $H_2O$) | >46 |  |  |  |
| Ex. 2 | 0.15 | Oemeta (4% in $H_2O$) | 30 | 34 |  | 38 |
| Ex. 3 | 0.15 | Oemeta (4% in $H_2O$) | >50 |  |  |  |
| Ex. 5 | 0.15 | Oemeta (4% in $H_2O$) | >46 |  |  |  |
| THT | 0.15 | Oemeta (4% in $H_2O$) | 10 | 15 |  | 18 |

[a]Dromus B (Trademark) - mineral oil based cooling-lubricant
Addix SF (Trademark) - synthetic cooling-lubricant
Oemeta 59 - mineral oil based cooling-lubricant The above results demonstrate the excellent antimicrobial activity of the compounds of Examples 1, 2, 3 and 5 and their superiority as antimicrobial agents over the known antimicrobial agent, trishydroxyethylhexahydrotriazine, which is prepared from monoethanolamine and formaldehyde in a manner analagous to the preparation of the compound of Example 1 but where the ethanolamine and formaldehyde are reacted in a ratio of 1:1.

In practicing the method of the invention the compounds can be prepared for use by mixing or dissolving in a suitable liquid carrier, e.g., as solutions in a solvent such as but not limited to water and alcohols.

The amount of the compounds or mixtures thereof to be incorporated in the material to be preserved and disinfected by the method of the invention will depend on various factors such as the nature of the material to be protected, and can readily be determined by one having ordinary skill in the art. Generally an amount will be incorporated which results in a concentration in the material to be protected of from about 0.1 to about 4 percent by weight.

We claim:

1. A method for preventing or retarding the growth of bacteria and fungi in a material susceptible to bacterial and fungal contamination which comprises treating the material with an antibacterially and antifungally effective amount of a compound of the formula

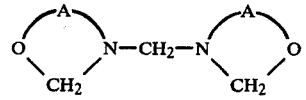

where A is 1,2-alkanediyl having from 2 to 10 carbon atoms.

2. A method according to claim 1 where A is 1,2-alkanediyl having from 2 to 4 carbon atoms.

3. A method according to claim 2 wherein the compound is selected from the group consisting of N,N'-methylenebis(oxazolidine), N,N'-methylenebis(5-methyloxazolidine), N,N'-methylenebis(4,4-dimethyloxazolidine) and N,N'-methylenebis(4-ethyloxazolidine).

* * * * *